United States Patent
Tsujii et al.

(10) Patent No.: US 9,245,659 B2
(45) Date of Patent: Jan. 26, 2016

(54) X-RAY IMAGING APPARATUS

(71) Applicants: Osamu Tsujii, Kawasaki (JP); Makoto Sato, Tokyo (JP); Masahiko Okunuki, Akiruno (JP); Satoshi Shimizu, Boca Raton, FL (US); Takashi Ogura, Tokyo (JP)

(72) Inventors: Osamu Tsujii, Kawasaki (JP); Makoto Sato, Tokyo (JP); Masahiko Okunuki, Akiruno (JP); Satoshi Shimizu, Boca Raton, FL (US); Takashi Ogura, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 62 days.

(21) Appl. No.: 13/937,268

(22) Filed: Jul. 9, 2013

(65) Prior Publication Data
US 2013/0294582 A1    Nov. 7, 2013

Related U.S. Application Data

(63) Continuation of application No. 13/125,862, filed as application No. PCT/JP2009/069406 on Nov. 9, 2009, now Pat. No. 8,509,387.

(30) Foreign Application Priority Data

Nov. 11, 2008   (JP) ................................. 2008-289173

(51) Int. Cl.
*G21K 1/04*    (2006.01)
*A61B 6/06*    (2006.01)
*A61B 6/00*    (2006.01)

(52) U.S. Cl.
CPC ... *G21K 1/04* (2013.01); *A61B 6/06* (2013.01); *A61B 6/4007* (2013.01);
(Continued)

(58) Field of Classification Search
CPC ........................................................ A61B 6/06
USPC .................................................. 378/146, 124
See application file for complete search history.

(56) References Cited

U.S. PATENT DOCUMENTS 6,055,292 A    4/2000   Zeller et al. ..................... 378/21
6,324,258 B1   11/2001  Beekman ....................... 378/145
(Continued)

FOREIGN PATENT DOCUMENTS

EP   1016375    7/2000
EP   1995757    11/2008
(Continued)

OTHER PUBLICATIONS

Korean Office Action dated Sep. 17, 2012 issued in counterpart application No. 10-2011-7012664.
(Continued)

*Primary Examiner* — Hoon Song
(74) *Attorney, Agent, or Firm* — Fitzpatrick, Cella, Harper & Scinto

(57) ABSTRACT

An X-ray imaging apparatus is provided with a multi X-ray source and a collimator in which a plurality of slits for X-rays to pass through are two-dimensionally formed, the size and position of the slits being adjustable. A control unit, as a first control mode, controls the size and position of the slits to move an examination region in parallel, when an X-ray source is changed to a different X-ray source, such that the examination directions are parallel before and after the change. Also, the control unit, as a second control mode, controls the size and position of the slits to rotate the examination direction, when an X-ray source is changed to a different X-ray source, such that the center of the examination regions is the same before and after the change.

12 Claims, 9 Drawing Sheets

(52) U.S. Cl.
CPC ............ *A61B 6/4405* (2013.01); *A61B 6/4441* (2013.01); *A61B 6/587* (2013.01); *G21K 1/046* (2013.01); *H01J 2235/068* (2013.01)

(56) References Cited

U.S. PATENT DOCUMENTS

| | | | |
|---|---|---|---|
| 6,435,713 B1 | 8/2002 | Iizuka | 378/195 |
| 7,187,756 B2* | 3/2007 | Gohno et al. | 378/124 |
| 8,509,387 B2* | 8/2013 | Tsujii et al. | 378/146 |
| 2002/0094064 A1 | 7/2002 | Zhou et al. | 378/122 |
| 2002/0196899 A1 | 12/2002 | Karellas | 378/98.8 |
| 2004/0213378 A1 | 10/2004 | Zhou et al. | 378/122 |
| 2007/0133749 A1 | 6/2007 | Mazin et al. | 378/149 |
| 2009/0232272 A1* | 9/2009 | Tsujii et al. | 378/16 |
| 2010/0098218 A1* | 4/2010 | Vermilyea et al. | 378/144 |
| 2012/0140895 A1 | 6/2012 | Okunuki et al. | 378/122 |

FOREIGN PATENT DOCUMENTS

| | | |
|---|---|---|
| GB | 2035769 | 6/1980 |
| JP | 55-60900 A | 5/1980 |
| JP | 1-254148 A | 10/1989 |
| JP | 5-269122 A | 10/1993 |
| JP | 7-067868 | 3/1995 |
| JP | 09-187447 | 7/1997 |
| JP | 2001-120526 | 5/2001 |
| JP | 2001-137221 | 5/2001 |
| JP | 2005-261838 | 9/2005 |
| JP | 2006-136500 | 6/2006 |
| JP | 2007-265981 | 10/2007 |
| KR | 1020070007512 | 1/2007 |
| WO | 2007/100105 | 9/2007 |

OTHER PUBLICATIONS

Russian Office Action dated Aug. 22, 2012 issued in the counterpart application No. 2011123731.

Extended European Search Report issued on Mar. 28, 2013 in counterpart European Patent application No. 09826176.1.

* cited by examiner

F I G. 1
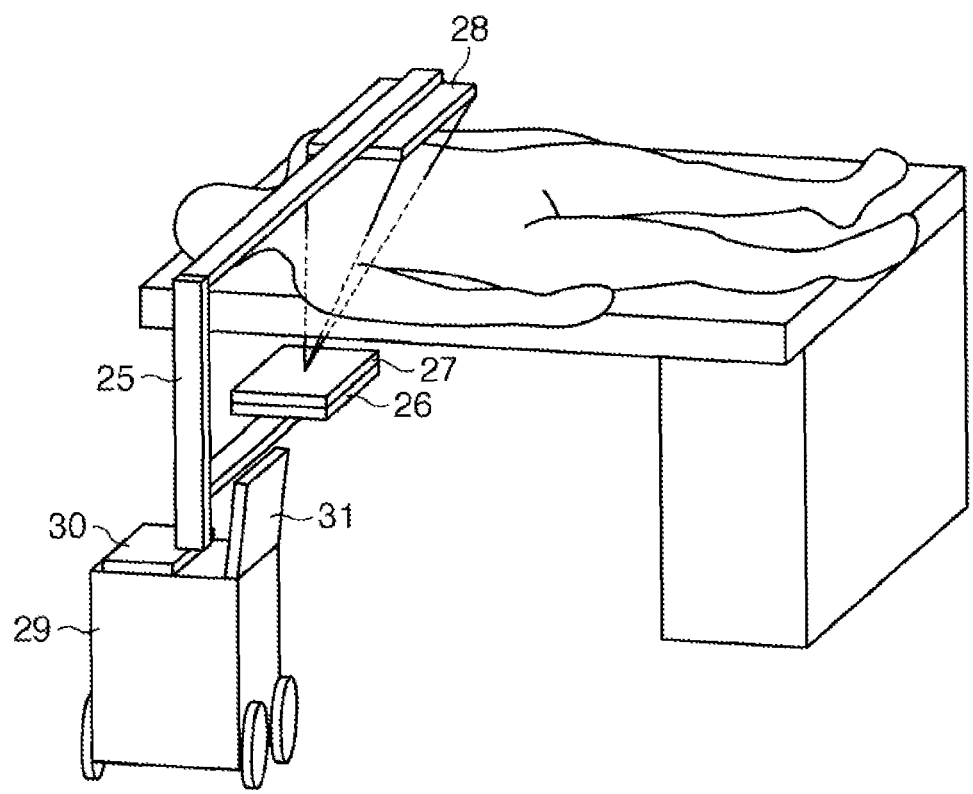

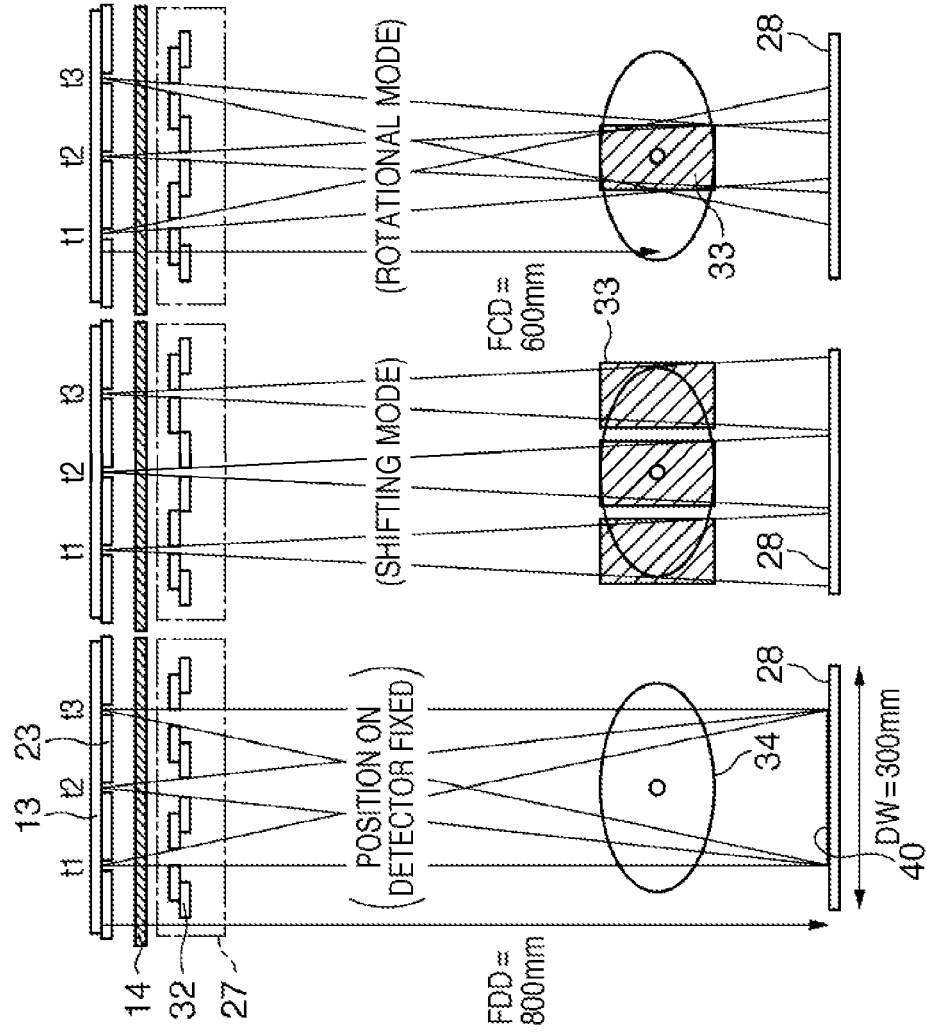

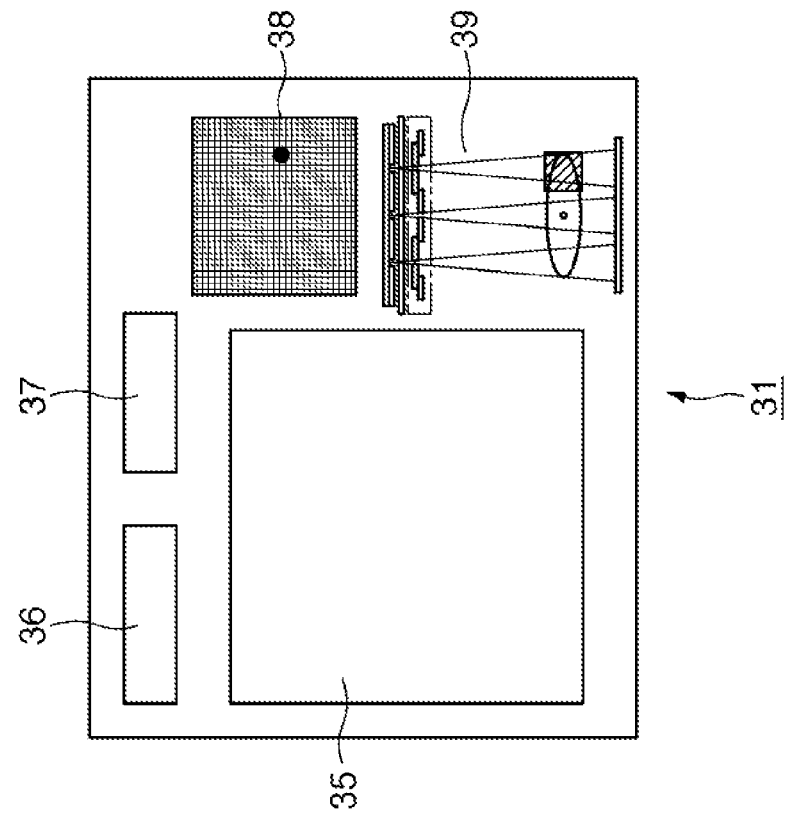
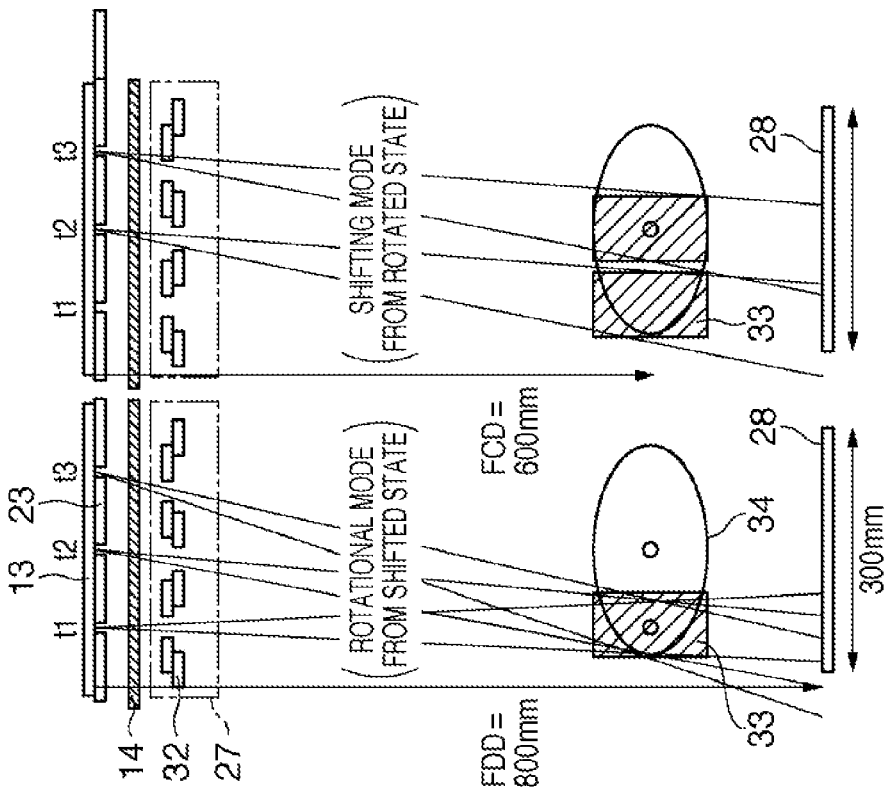

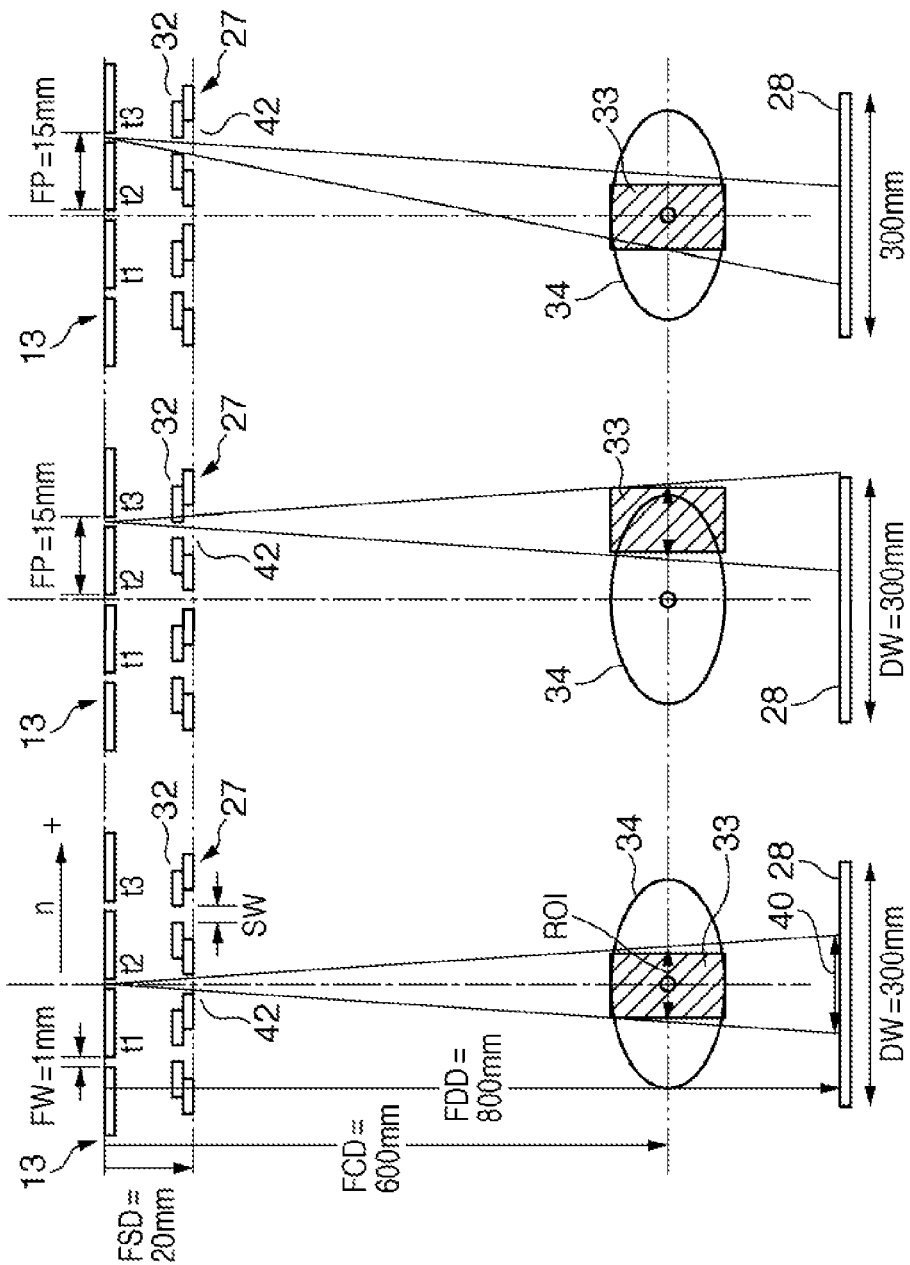

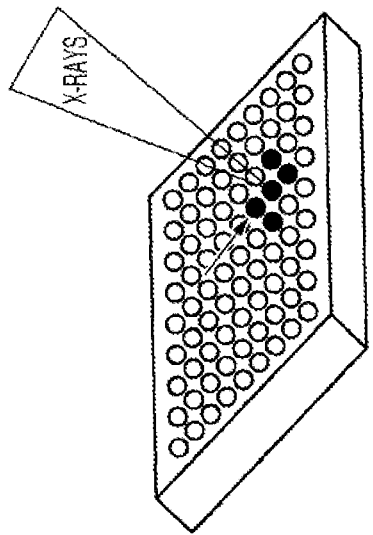
FIG. 9A
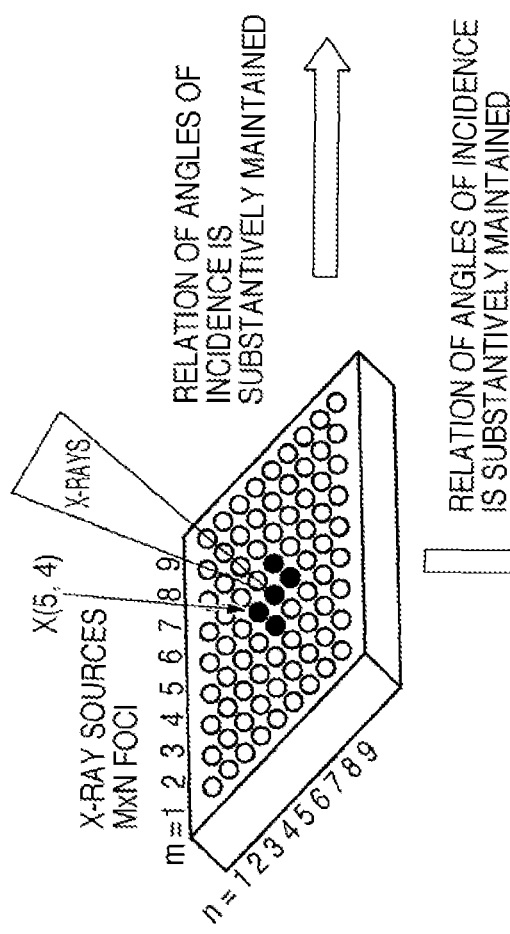
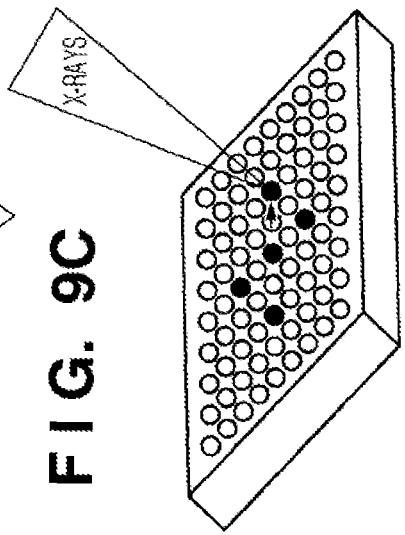
FIG. 9B
FIG. 9C

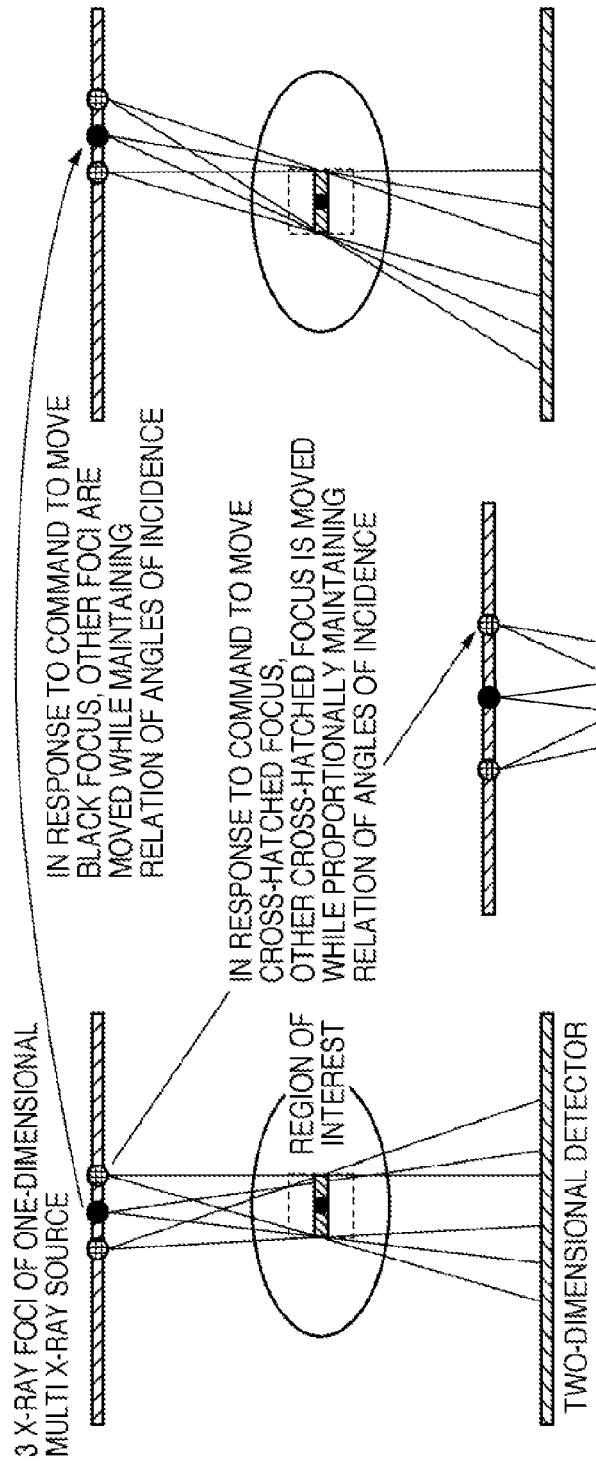

X-RAY IMAGING APPARATUS

CROSS REFERENCE TO RELATED APPLICATIONS

This application is a continuation of U.S. application Ser. No. 13/125,862, which is a national phase application under 35 U.S.C. §371 based on International Application No. PCT/JP2009/069406, filed on Nov. 9, 2009, and claims the benefit of Japanese Patent Application No. 2008-289173, filed Nov. 11, 2008. Each of those applications is hereby incorporated by reference herein in its entirety.

TECHNICAL FIELD

The present invention relates to an X-ray imaging apparatus, and more particularly to an X-ray imaging apparatus that selectively uses a plurality of X-ray sources to provide an X-ray fluoroscopic image.

BACKGROUND ART

International Publication WO/2007/100105 discloses a technique for producing a multi X-ray beam by distributing electron sources two-dimensionally and controlling the electron sources individually. The divergence angle of the multi X-ray beam is determined by the opening conditions of X-ray extraction windows disposed in a vacuum.

However, there are cases where it is desirable to adjust the divergence angle of the multi X-ray beam depending on the imaging conditions. To accommodate this, in International Publication WO/2007/100105, a vacuum X-ray shielding plate 23 is added as a first shielding plate, and combined with an atmospheric X-ray shielding plate 41 constituting a second shielding plate. The divergence angle of the multi X-ray beam can be freely selected in accordance with the irradiation conditions of the object, given that this second shielding plate provided in air can be easily replaced.

Japanese Patent Laid-Open No. 09-187447 discloses a movement mechanism for moving the distance between two X-ray tubes (foci) or the interfocus distance of one X-ray tube, based on information on an imaging magnification factor or imaging geometry for stereo imaging. Japanese Patent Laid-Open No. 09-187447 further discloses providing another movement mechanism that enables adjustment of an X-ray aperture, such that an appropriate X-ray exposure range can be set in response to driving of the above movement mechanism.

Japanese Patent Laid-Open No. 2006-136500 discloses a movement mechanism of a movable aperture device moving aperture blades to a prescribed position based on information on an imaging range and forming a diagnostic imaging region, in a fluoroscopic imaging apparatus. Herein, the state of the aperture blades in the case where a monitoring imaging region is formed, and the state of the aperture blades in the case where a diagnostic imaging region is formed are disclosed. The four aperture blades move at high speed when generating monitoring image data, as a result of an aperture movement control unit receiving arrival signals from a pixel value comparing unit, and form a diagnostic imaging region.

Japanese Patent Laid-Open No. 2001-120526 discloses an X-ray fluoroscopic apparatus provided with a cradle for the patient to lie down on, and a first X-ray tube and a semiconductor detector that are respectively attached to first and second ends of a C-arm whose arms are capable facing one another with the cradle therebetween. This apparatus is equipped with a second X-ray tube that is positioned further away than the distance from the semiconductor detector to the first X-ray tube. Further, this apparatus is also equipped with semiconductor detector movable supporting means for movably supporting the semiconductor detector so as to be capable of taking a first position or orientation facing the first X-ray tube and a second position or orientation facing the second X-ray tube.

Japanese Patent Laid-Open No. 2001-137221 discloses a CT gantry provided with two angiographic arms in addition to a CT imaging X-ray tube and an X-ray detector. One angiographic arm is a frontal arm provided with an X-ray tube and an X-ray image receiving device for performing vertical angiography of a sample. The other angiographic arm is a lateral arm provided with an X-ray tube and an X-ray image receiving device for performing horizontal angiography of a sample. According to Japanese Patent Laid-Open No. 2001-137221, the CT gantry is removed to a position that does not obstruct the angiography, and the frontal arm and the lateral arm are moved to an angiography position, based on an instruction from an operator. Also, the frontal arm and the lateral arm can be removed to a position that does not obstruct the CT imaging, based on an instruction from an operator.

In the operating room, the surgeon moves the C-arm device himself or herself to locate the best angle. The surgeon needs to perform fine positional setting of the entire C-arm device. The present invention is premised on applying an X-ray imaging apparatus having a plurality of X-ray sources (multi X-ray source, MBX), in order to facilitate this positional setting.

Specifically, the following three types of changes to the examination region are available, in the case where fluoroscopy is performed after narrowing the examination region with an X-ray aperture in order to reduce radiation exposure to the patient.

The first involves scaling the examination area, the second involves shifting the examination region, and the third involves changing the examination direction.

A plurality of aperture units need to be changed in conjunction with each of these three types of changes to the examination region. In the case of shifting the examination region, it is considered necessary to maintain the examination direction and also preferably the examination area, and in the case of changing the examination direction, it is considered necessary to maintain the examination center and also preferably the examination area.

However, as for conventional apparatuses that use a plurality of X-ray sources, there are only commonly known examples of a stereo imaging apparatus and a double C-arm device, as described above, and there is no known technology of a C-arm device that uses a multi X-ray source. Therefore, there is no recognition of the above problems, and consequently no technique for solving these problems.

On the other hand, there are cases where it is desirable to use a plurality of X-ray sources to examine a plurality of examination areas substantially at the same time (or sequentially). In these cases, it is envisioned that it may be desirable to change the selection of one X-ray source in response to a change in the selection of another X-ray source. However, there is currently no technique for meeting such a requirement.

DISCLOSURE OF INVENTION

The present invention solves at least one of the above problems.

An X-ray imaging apparatus according to one aspect of the present invention includes a multi X-ray source having a plurality of X-ray sources arranged two-dimensionally, an X-ray detector having a plurality of detecting elements two-dimensionally arranged facing the multi X-ray source, and a collimator provided between the multi X-ray source and the X-ray detector, for restricting an irradiated area of X-rays from the multi X-ray source. The collimator is configured to form a plurality of slits through which X-rays pass, such that the plurality of slits being two-dimensionally arrayed in correspondence with the plurality of X-ray sources. The collimator is further configured to be capable of adjusting a size and a position of the plurality of slits. Selecting means selects one or more X-ray sources for performing X-ray irradiation, from the plurality of X-ray sources, in order to select an examination region of an object. Control means controls the size and the position of the plurality of slits of the collimator according to the selection by the selecting means. The control means has a first control mode for controlling, when there is a change to a different X-ray source by the selecting means, the size and the position of the plurality of slits to move the examination region in parallel, such that examination directions before and after the change are parallel, and a second control mode for controlling, when there is a change to a different X-ray source by the selecting means, the size and the position of the plurality of slits to rotate the examination direction, such that a center of the examination regions before and after the change is the same.

Further features of the present invention will become apparent from the following description of exemplary embodiments with reference to the attached drawings.

BRIEF DESCRIPTION OF DRAWINGS

FIG. 1 shows an exemplary C-arm device according to an embodiment.

FIGS. 2A to C illustrate control of a collimator in the embodiment.

FIGS. 4A and B illustrate control of a collimator in a case where a shifting mode and a rotational mode are combined in the embodiment.

FIG. 5 shows an exemplary display screen configuration of a display in the embodiment.

FIGS. 6A to C illustrate a control method of a collimator in the embodiment.

FIGS. 9A to C illustrate an X-ray source selection method in a second embodiment.

FIGS. 10A to C illustrate a relation of imaged images in the second embodiment.

BEST MODE FOR CARRYING OUT THE INVENTION

Figure 3A:
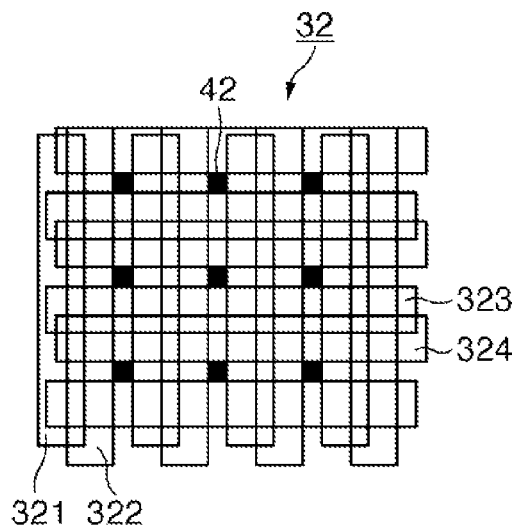
FIGS. 3A to D show an exemplary structure of aperture plates in the embodiment.

Various exemplary embodiments, features, and aspects of the present invention will be described in detail below with reference to the drawings.

First Embodiment

A preferred embodiment of the present invention will be described in detail with reference to FIG. 1 to FIG. 8.

FIG. 1 shows a scene in which an X-ray fluoroscopic image of a body is imaged with a C-arm device serving as an X-ray imaging apparatus according to the present embodiment.

A two-dimensional detector 28 and a multi X-ray source 26 are fixed to a C-arm 25. A collimator 27 as an X-ray aperture is fixed to an irradiation side of the multi X-ray source 26.

The multi X-ray source 26, which has a plurality of two-dimensionally arranged X-ray sources, or more specifically, N×M X-ray foci, is provided on the underside of the patient, for example. X-rays discharged from a transmission target 13 (X-ray focus) of the multi X-ray source 26 (described below) arrive at the two-dimensional detector 28 after passing through the body. The two-dimensional detector 28 is an X-ray detector having a plurality of detecting elements two-dimensionally arranged facing the multi X-ray source. The intensity distribution of X-rays reaching the two-dimensional detector 28 is displayed as an X-ray fluoroscopic image on a display 31.

A control panel 30 is connected to a control unit 29. The control unit 29 is able to select an X-ray focus for performing exposure from out of the N×M X-ray foci, and change the X-ray fluoroscopic image on the display 31 based on an image read out from the two-dimensional detector 28, in accordance with operation of the control panel 30 by a doctor. Also, the irradiation area and the irradiation angle can be changed as a result of an X-ray focus for performing exposure being selected from the N×M X-ray foci and the corresponding collimator 27 changing, in response to a command from the control panel 30.

Figure 8:
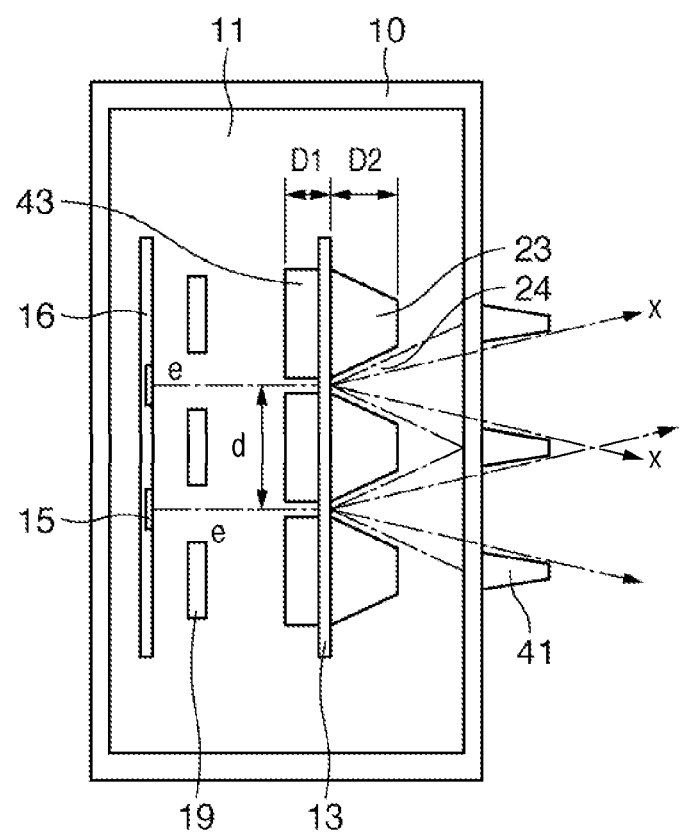
FIG. 8 shows an exemplary structure of a multi X-ray source.

The structure of the multi X-ray source 26 will be described using FIG. 8. Note that FIG. 8 is the same as a figure disclosed in International Publication WO/2007/100105.

Electrons are emitted from one of multi-electron emitting elements 15 configured on an electron array 16. Emitted electrons hit the transmission target 13 after being shaped by a lens electrode 19 and accelerated by an acceleration electric field. X-rays transmitted from the transmission target 13 are directionally restricted by a vacuum X-ray shielding plate 23. Note that while in FIG. 8, transmitted X-rays are further directionally restricted using an atmospheric X-ray shielding plate 41, whereas in the present embodiment, the portion corresponding to the atmospheric X-ray shielding plate 41 is replaced by the collimator 27.

The collimator 27 is provided between the multi X-ray source 26 and the two-dimensional detector 28, and is for restricting the irradiated area of X-rays from the multi X-ray source 26. With this collimator 27, a plurality of slits 42 for X-rays to pass through are formed two-dimensionally in correspondence with the plurality of X-ray sources in the multi X-ray source 26, using a plurality of aperture plates 32, as shown in FIGS. 3A to D. The size and position of the plurality of slits 42 are adjustable by controlling the aperture plates 32.

Control of the collimator 27 constituting a main portion of the present embodiment will be described using FIGS. 2A to C.

Description is limited to one dimension in FIGS. 2A to C because action is independent between dimensions even if the figures were expanded to two dimensions. The figures can be easily expanded from one dimension to two dimensions.

Figure 3B:
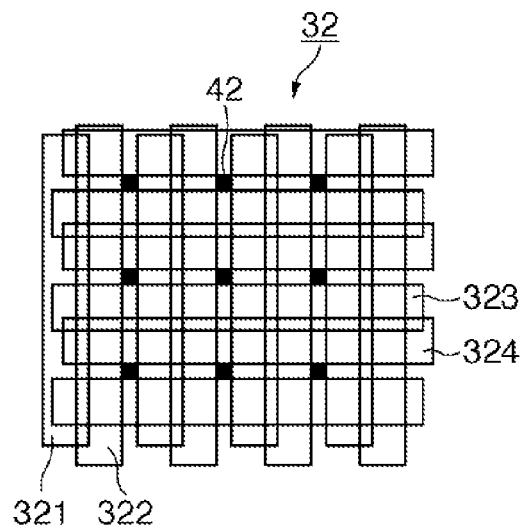
Figure 3C:
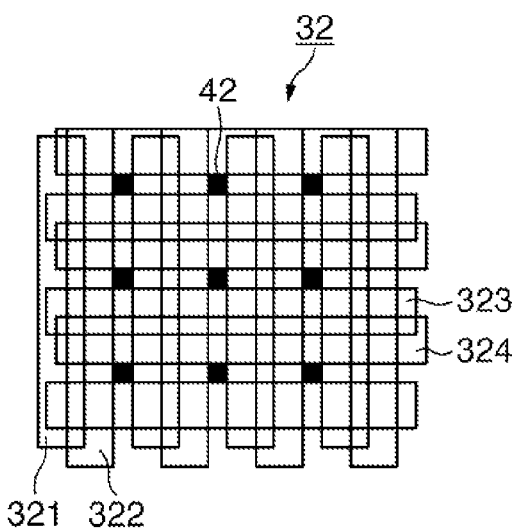
Figure 3D:
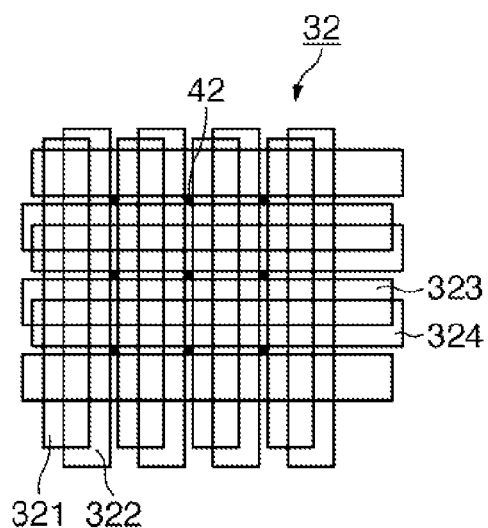

FIG. 2A shows an example in which the aperture plates 32 of the collimator 27 are controlled such that the X-ray sources constituting the multi X-ray source 26 have irradiation regions in the same place on the two-dimensional detector 28. The aperture plates 32 are members for shielding X-rays, and are manufactured from tungsten, lead, copper, iron, or an alloy thereof, for example. In the present embodiment, the aperture plates 32 are constituted by four types of aperture plate denoted by 321, 322, 323 and 324, as shown in FIGS. 3A to C. That is, the collimator 27 is constituted by a set of aperture plates and a drive mechanism (not shown) that drives these aperture plates.

Control of the collimator 27 such that a light-receiving region 40 is in the same place on the two-dimensional detector 28, as shown in FIG. 2A, may be clinically inconvenient for the following reasons.

For example, assume that when examining an object 34 with X-rays from a target t2 constituting the X-ray source, the physician wants to examine the right side of the object 34. The physician, in order to select an examination region of the object, is able to select one or more X-ray sources for performing X-ray irradiation from the plurality of X-ray sources, using the control panel 30, and further issue a request to switch the X-ray sources.

While examination of the right side region of the object 34 does become possible once the target constituting the X-ray source is switched from t2 to t3 in response to this request, the examination direction (examination angle) of the object 34 is changed. This change in the examination direction is not what the doctor wanted.

Similarly, assume that when examining the object 34 with X-rays from the target t2, the physician wants to examine the object 34 after rotating the observation direction to the right side. While examination of an image obtained after rotating the observation direction of the object 34 to the right side does become possible once the target constituting the X-ray source is switched from t2 to t3 in response to this request, the examination region 33 and the examination center of the object 34 are changed. This change in the examination region 33 and the examination center is not what the doctor wanted.

Control of the collimator 27 in a shifting mode will be described using FIG. 2B.

In the shifting mode (first control mode), the aperture plates 32 are controlled such that the examination regions 33 formed by a target ti and another target tj are in a relation where the examination region 33 shifts while maintaining the examination direction (moves horizontally). In other words, when the X-ray source for performing X-ray irradiation is changed to a different X-ray source, the size and position of the plurality of slits 42 are controlled to move the examination region in parallel, such that the examination directions before and after the change are parallel.

Because the examination area preferably is also maintained in addition to the examination direction with control in the shifting mode, control for maintaining both the examination direction and the examination area will be described in the present embodiment.

With the C-arm device according to the present embodiment, there is a rotational mode in additional the shifting mode. Switching between the shifting mode and the rotational mode can be performed by operation of the control panel 30. In the shifting mode, when the aperture plate 32 facing the target t2 is controlled in order for the physician to scale the examination region 33, in the case where the physician is examining the object 34 with X-rays from the target t2, the aperture plates 32 facing the other targets t1 and t3 are also scaled in conjunction with this control. Similarly, in the shifting mode, when the aperture plate 32 facing the target t3 is controlled in order for the physician to scale the examination region 33, in the case where the physician is examining the object 34 with X-rays from the target t3, the aperture plates 32 facing the other targets t1 and t2 also change in conjunction with this control.

Control of the collimator 27 in the rotational mode will be described using FIG. 2C.

In the rotational mode (second control mode), the aperture plates 32 are controlled such that the examination regions 33 formed by a target ti and another target tj are in a relation where the examination direction is rotated while maintaining the examination center. In other words, when the X-ray source for performing X-ray irradiation is changed to a different X-ray source, the size and position of the plurality of slits 42 are controlled to rotate the examination direction, such that the center of the examination regions before and after the change is the same. It is additionally desirable to also maintain the examination area so as to be constant. Here, maintaining both the examination center and the examination area will be referred to as "maintaining the examination region 33".

In the rotational mode, when the aperture plate 32 facing the target t2 is controlled in order for the physician to scale the examination region 33, in the case where the physician is examining the object 34 with X-rays from the target t2, the aperture plates 32 facing the other targets t1 and t3 are also scaled in conjunction with this control. Because the interval between the transmission targets 13 is physically fixed, the amount of change in the examination direction can be calculated by hypothetically setting the distance (FCD: Focus Center Distance) from the transmission target in the center of the multi X-ray source 26 to the center of the object 34. In the present embodiment, the FCD can be input from the control panel 30.

FIGS. 3A to D show an exemplary structure of the aperture plates 32.

FIGS. 3A and B show an example where the irradiation field is scaled down in the shifting mode. With the change from FIGS. 3A to B, only the areas of the slits 42 are scaled down, and the distance relation between the centers of the slits 42 remains unchanged.

FIGS. 3C and D show an example in which the irradiation field is scaled down in the rotational mode. With the change from FIGS. 3C to D, the distance relation between the centers of the slits 42 changes at the same time, when only the areas of the slits 42 are scaled down.

Control of the collimator 27 in the case where the shifting mode and the rotational mode are combined will be described using FIGS. 4A and B.

FIG. 4A shows the case of switching from the shifting mode to the rotational mode. Assume the case of changing to the rotational mode during examination of a portion of the object 34 using the target t1 under control in the shifting mode. In this case, the other targets t2 and t3 are controlled such that the examination direction rotates while maintaining the examination region 33, as shown in FIG. 4A.

FIG. 4B shows the case of changing to the shifting mode during examination of a portion of the object 34 using the target t3 under control in the rotational mode. In this case, the other targets t1 and t2 are controlled such that the examination region 33 shifts while maintaining the examination direction, as shown in FIG. 4B.

There are some problems to be aware of in FIGS. 4A and B. X-rays that pass through the collimator 27 may extend beyond the surface of the two-dimensional detector 28 when the collimator 27 is set so as to satisfy each mode. In this case the patient is unnecessarily exposed to radiation. In order to inhibit such unnecessary radiation exposure, the collimator 27 is controlled such that X-rays do not extend beyond the two-dimensional detector 28. In other words, the collimator 27 is controlled such that X-rays irradiated from the multi X-ray source 26 are all projected onto the two-dimensional detector 28.

The C-arm device according to the present embodiment is able to repeatedly select transmission targets 13 and switch between the shifting mode and the rotational mode indefinitely.

The C-arm device according to the present embodiment has the transmission target 13 selected by an operator, the examination region 33 formed by the selected target, and the display 31 for informing the operator of the examination direction.

FIG. 5 shows an exemplary display screen structure of the display 31.

The display 31 is constituted by a liquid crystal display or the like. An image display portion 35 displays an image imaged with X-rays from the currently selected transmission target 13. A patient information display 36 and an image processing information display portion 37 for displaying window information and the like are arranged above the image display portion 35. A target display portion 38 is for displaying the selected target, and displays the position, on the entire multi beam X-ray source, of the transmission target 13 currently selected by the operator. An examination region/direction display portion 39 is for displaying the examination region 33 and examination direction of the object 34, and displays the examination region 33 and the examination direction in the case where a hypothetical object 34 is assumed, as cross-sectional information. The hypothetical object 34 is calculated using the FCD (Focus Center Distance) input from the control panel 30.

Next, an operation for resetting the collimator 27 will be described.

As described above, the C-arm device in the present embodiment is able to repeatedly select transmission targets 13 and switch between the shifting mode and the rotational mode indefinitely. However, when the examination direction at a peripheral transmission target 13 is set at a large angle, X-rays formed by another target may not form an image on the two-dimensional detector 28. In this case, the operator preferably is able to return the collimator 27 to a reset state. The collimator 27 also needs to be returned to a reset state if the object 34 (patient) is changed.

The reset state of the collimator 27 can be set by the operator. Exemplary reset states of the collimator 27 include the states of FIGS. 2B and C.

Next, a method of controlling the collimator 27 using the position and size of the slits 42 rather than the movement of the aperture plates 32 shown in FIGS. 4A and B will be described with reference to FIGS. 6A to C. While this will be described in one dimension, calculations can be performed two-dimensionally for each axis independently.

FDD (Focus Detector Distance) is the length of a vertical line from the transmission targets 13 of the multi X-ray source 26 down to the two-dimensional detector 28. FCD (Focus Center Distance) is the distance from the transmission target 13 positioned in the center of the multi X-ray source 26 to the center of a hypothetical object. FSD (Focus Slit Distance) is the distance from the transmission targets 13 to the slits 42. Also, the relation of an equation (1) is satisfied, where FW (Focus Width) is the width of the transmission targets 13, SW (Slit Width) is the width of the slits 42, and ROI (Region Of Interest) is the width of the examination region 33. Note that SW≥FW is assumed.

$$ROI = (FW + SW) \cdot (FCD/FSD) - FW \quad (1)$$

Because FW of the equation (1) is very small relative to the second term, the equation (1) can be approximated as in an equation (2).

$$ROI \approx (FW + SW) \cdot (FCD/FSD) \quad (2)$$

Transforming the equation (2) enables the width SW of the slits 42 when the ROI has been determined by the operator to be calculated by an equation (3).

$$SW = ROI \cdot (FSD/FCD) - FW \quad (3)$$

If the control mode of the collimator 27 is the shifting mode, the width $SW(t0)$ of the slit 42 facing a target t0 being examined by the operator will equal the width $SW(tn)$ of the slit 42 facing a target tn positioned n targets away, as in the equation (4).

$$SW(t0) = SW(tn) \quad (4)$$

If the control mode is the shifting mode, the relation of an equation (5) is satisfied between a position $P(SW(t0))$ of the slit 42 facing the target t0 being examined by the operator and a position $P(SW(tn))$ of the slit 42 facing the target tn positioned n targets away. Here, FP (Focus Pitch) is the pitch of transmission targets 13. FIG. 6B represents the relation between the equation (4) and the equation (5).

$$P(SW(tn)) = P(SW(t0)) + n \cdot FP \quad (5)$$

If the control mode of the collimator 27 is the rotational mode, the width $SW(t0)$ of the slit 42 facing a target t0 being examined by the operator and the width $SW(tn)$ of the slit 42 facing a target tn positioned n targets away will be equal, as in the equation (6).

$$SW(t0) = SW(tn) \quad (6)$$

If the control mode of the collimator 27 is the rotational mode, the relation of an equation (7) is satisfied between a position $P(SW(t0))$ of the slit 42 facing the target t0 being examined by the operator and the position $P(SW(tn))$ of the slit 42 facing a target tn positioned n targets away. FIG. 6C represents the relation between the equation (6) and the equation (7).

$$P(SW(tn)) = P(SW(t0)) + n \cdot FP \cdot ((FCD - FSD)/FCD) \quad (7)$$

FCD defines the distance from the transmission target 13 positioned in the center of the multi X-ray source 26 to the center of a hypothetical object. If the placement of the actual object 34 differs from the FCD stored by the C-arm device, the values calculated by the above equations (1) to (7) will not coincide with the operator's expectations. In view of this, the FCD value can be changed from the control panel 30 at any time.

Next, a technique for making the examination centers coincide in response to the switching of a plurality of X-ray sources under control in the rotational mode will be described.

As described above, the collimator 27 is controlled such that the centers of the examination regions 33 (examination centers) coincide in the rotational mode. The region on the two-dimensional detector 28 in the case where X-rays are projected onto the examination region 33 is a light-receiving region 40 (see FIG. 6A).

If the slit 42 is positioned in front of the transmission target 13, the light-receiving region 40 will be rectangular. Here, the slits 42 are rectangular, and "in front of" denotes a vertical line from the center of a transmission target 13 down to the plane of the collimator 27 passing through the center of a slit 42 (see light-receiving region 40 from X-ray source t0 in FIG. 7A). If the slit 42 is not positioned in the front of the transmission target 13 (this is called oblique incidence), the light-receiving region 40 will be a quadrilateral other than a square or rectangle.

Figure 7B:
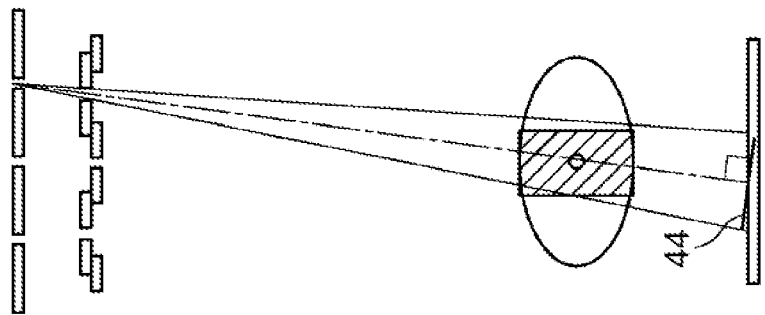
FIGS. 7A and B illustrate an affine transform of an image at oblique incidence in the embodiment.
Figure 7A:
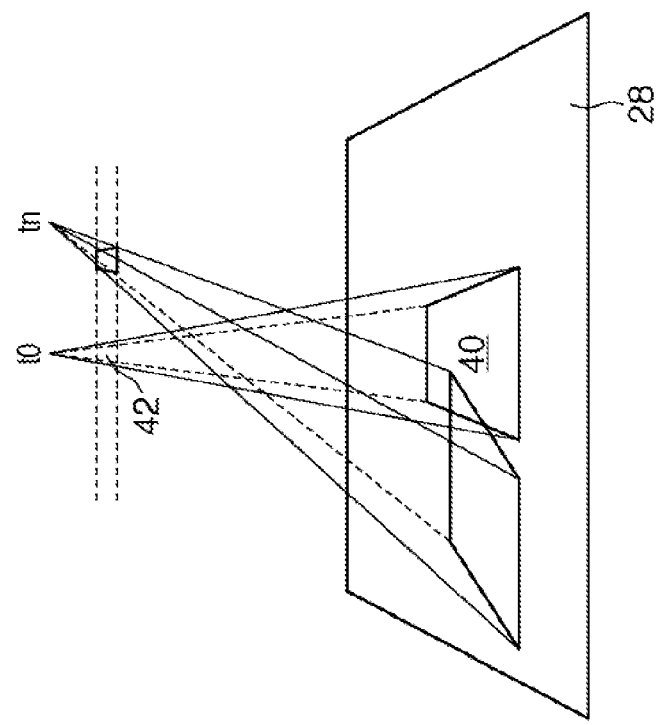

On the other hand, in the rotational mode, it is appropriate to perform image display such that that the transmission target 13 for discharging X-rays is orthogonal to the light beam that passes through the center of the examination region 33. In view of this, images are affine-transformed (projected) from the two-dimensional detector 28, assuming an affine transform plane 44 such as shown in FIG. 7B. The affine transform plane 44 is orthogonal with a line connecting the X-ray source for discharging X-rays and the center of the examination region 33, and includes the point at which this line intersects the two-dimensional detector 28.

There are two methods for clipping the light-receiving region 40 from an image read out from the two-dimensional detector 28. One method involves clipping the light-receiving region 40 using X-ray signal values. The other method involves deriving the light-receiving region 40 on the two-dimensional detector 28 from the position and area of the slits 42 of the collimator 27 by calculations. The light-receiving region 40 clipped with either method is displayed on the display 31 after having an affine transform applied thereto. If the calculation time of the affine transform is short, the light-receiving region 40 can be clipped after the entire image from the two-dimensional detector 28 has been affine-transformed. If the calculation time of the affine transform is long, the affine transform is preformed after clipping a partial image from the two-dimensional detector 28, so as to include the light-receiving region 40. Affine-transformed images obtained by the above processing will have coinciding examination centers.

In order to inhibit unnecessary radiation exposure to the patient, the collimator 27 is controlled such that X-rays do not extend beyond the two-dimensional detector 28 (are not vignetted). The position and area of the slits 42 of the collimator 27 are calculated in accordance with each mode of the collimator 27. The light-receiving region 40 on the two-dimensional detector 28 is derived by calculations from the calculated position and area of the slits 42. The width of the light-receiving region IRA (Irradiation Area) in the case of the control mode of the collimator 27 being the shifting mode is calculated by an equation (8).

$$IRA=(FW+SW)\cdot(FDD/FSD) \quad (8)$$

If the control mode of the collimator 27 is the shifting mode, the relation of an equation (9) is satisfied between a position P(IRA(t0)) of the light-receiving region 40 formed by a target t0 being examined by the operator and a position P(IRA(tn)) of the light-receiving region 40 formed by a target tn positioned n targets away.

$$P(IRA(tn))=P(IRA(t0))+n\cdot FP \quad (9)$$

The light-receiving region 40 will extend beyond the two-dimensional detector 28 if an equation (10) is satisfied, where DW (Detector Width) is the width of the two-dimensional detector 28, and assuming that P(IRA(t0)) coincides with the center of the two-dimensional detector 28. The aperture plates 32 are controlled such that the equation (10) has equality.

$$IRA(tn)/2+n\cdot FP \geq DW/2 \quad (10)$$

The light-receiving region IRA (Irradiation Area) in the case of the control mode of the collimator 27 being the rotational mode is calculated by an equation (11).

$$IRA=(FW+SW)\cdot(FDD/FSD) \quad (11)$$

If the control mode is the rotational mode, the relation of an equation (12) is satisfied between a position P(IRA(t0)) of the light-receiving region 40 formed by a target t0 being examined by the operator and a position P(IRA(tn)) of the light-receiving region 40 formed by a target tn positioned n targets away.

$$P(IRA(tn))=P(IRA(t0))+n\cdot FP\cdot(FDD-FCD)/FCD \quad (12)$$

The light-receiving region 40 will extend beyond the two-dimensional detector 28 if an equation (13) is satisfied, assuming that P(IRA(t0)) coincides with the center of the two-dimensional detector 28. The aperture plates 32 are controlled such that the equation (13) has equality.

$$IRA(tn)/2+n\cdot FP\cdot(FDD-FCD)/FCD \geq DW/2 \quad (13)$$

The first embodiment of the present invention is as described above.

In the related art, there is no technique, such as described above, where in conjunction with the change of one aperture in a multi X-ray source, another aperture is changed. The provision of two modes for changing the apertures in conjunction with one another, the first mode being for shifting the examination region, and the second mode being for rotating the examination direction, is also not disclosed in the related art.

In contrast, according to the present embodiment, images in which the center of the examination region (examination center) and the examination area are maintained, in the case where the object 34 is fluoroscopically examined while changing the examination direction, can be provided instantaneously.

Also, the patient is not subjected to unnecessary radiation exposure, because the examination center and the examination area are suitably changed prior to changing the examination direction.

Further, the examination region is easily changed, and a shortening of the operation time and a reduction of radiation exposure to the patient can be anticipated.

Second Embodiment

Hereinafter, a second embodiment will be described. The configuration of the C-arm device of the second embodiment is similar to the configuration shown in FIG. 1. Hereinafter, control of a collimator 27 will not be described in detail. The collimator 27 is controlled in two control modes, namely, a shifting mode and a rotational mode, similarly to the above-mentioned first embodiment, but the present embodiment is not limited to these two control modes.

Features of the present embodiment will be described using FIGS. 9A to C and FIGS. 10A to C.

FIG. 9A shows an example in which a body is imaged after selecting five X-ray sources indicated with black circles in a two-dimensional multi X-ray source. The two-dimensional multi X-ray source in FIG. 9A is constituted by a total of 81 X-ray sources arranged in a 9×9 array. The selected X-ray sources, expressed in the format X(m,n), are X(5,4), X(4,5), X(5,5), X(6,5) and X(5,6).

Rather than the five selected X-ray sources performing exposure simultaneously, only one X-ray source performs exposure at any one time. Conceivable methods of switching the X-ray source for performing exposure include the X-ray sources being switched periodically using a timer built into in a control unit, or being switched non-periodically by an operator.

An X-ray image resulting from exposed X-rays is displayed on a display. Methods of displaying images resulting from a plurality of X-rays include displaying all selected X-ray images or displaying only images resulting from recently exposed X-rays.

FIG. 9B illustrates an X-ray source selection change in a mode for substantively maintaining the relation of the angles of incidence of currently selected X-ray sources (relation maintaining mode). Switching between the relation maintaining mode and a mode for substantively proportionally maintaining the relation of the angles of incidence of X-ray sources as illustrated in FIG. 9C is performed by an instruction of an operator from a control panel.

A control panel 30 is able to receive, when at least two X-ray sources for performing X-ray irradiation are selected from a plurality of X-ray sources, an instruction to change a first X-ray source out of the at least two X-ray sources to a second X-ray source at another position.

In the case of the relation maintaining mode, when the X-ray source X(5,4) selected in FIG. 9A is changed to X(6,6), the other X-ray sources are respectively changed as follows: X(4,5)→X(5,7), X(5,5)→X(6,7), X(6,5)→X(7,7) and X(5,6)→X(6,8). In other words, in the case of the relation maintaining mode, when selection is, changed from one currently selected X-ray source X(m1,n1) to X(m1+Δm,n1+Δn), another currently selected X-ray source X(m2,n2) is changed to X(m2+Δm,n2+Δn), such that the relative positional relation of the selected X-ray sources prior to the change is maintained.

The change in the X-ray images imaged in the case of the relation maintaining mode is as shown in FIGS. 10A to C.

FIGS. 10A to C show the case of a one-dimensional multi X-ray source for simplicity. In FIG. 10A, three X-ray sources are selected. When selection the black X-ray source in the middle of the three selected X-ray sources in FIG. 10A is changed to the X-ray source on the right, selection of the other X-ray sources on either side is changed so as to substantively maintain the angles of incidence (FIG. 10B).

Looking at the relation between an X-ray image resulting from the three X-ray sources selected in FIG. 10B and an X-ray image resulting from the three X-ray sources selected in FIG. 10A, the angles of incidence relative to the region of interest are changed. However, the relation of the angles of incidence of the three selected X-ray sources is substantively maintained. Here, "substantively maintained" denotes the following. If the X-ray sources in the multi X-ray source are arranged equidistantly, the relation of the angles of incidence before and after the selection change cannot be made to completely coincide. However, if the X-ray source arrangement pitch of the multi X-ray source is very small compared with the distance from the multi X-ray source to the object, the difference in the relation of the angles of incidence before and after the selection change can be disregarded. This is referred to as being "substantively maintained."

FIG. 9C shows an X-ray source selection change in the mode for substantively proportionately maintaining the angles of incidence (proportion maintaining mode). In the case of the proportion maintaining mode, when the X-ray source X(6,5) selected in FIG. 9A is changed to X(7,5), the remaining X-ray sources are respectively changed as follows: X(5,4)→X(5,3), X(4,5)→X(3,5), and X(5,6)→X(5,7). Here, X(5,5) is a fixed reference X-ray source.

In other words, in the case of the proportion maintaining mode, when one currently selected X-ray source X1 is changed to X1', another currently selected X-ray source Xn is changed to Xn', where the fixed reference X-ray source is X0. That is, the other X-ray source is changed to an X-ray source at a position where the relative positional relation of the at least two X-ray sources before the change is scaled. Here, the displacement from the X-ray source X1 to X1' is expressed as follows.

$$\overrightarrow{X1X1'}$$

If this is the case, the following equations (14) and (15) are satisfied.

$$|\overrightarrow{X1X1'}| = |\overrightarrow{XnXn'}| \tag{14}$$

$$\frac{\overrightarrow{X0X1} \cdot \overrightarrow{X0X1'}}{|\overrightarrow{X0X1}| * |\overrightarrow{X0X1'}|} = \frac{\overrightarrow{X0Xn} \cdot \overrightarrow{X0Xn'}}{|\overrightarrow{X0Xn}| * |\overrightarrow{X0Xn'}|} \tag{15}$$

The change in the X-ray images imaged in the case of the proportion maintaining mode is shown in FIGS. 10A to C.

FIGS. 10A to C show the case of a one-dimensional multi X-ray source for simplicity. In FIG. 10A, three X-ray sources are selected. When selection of the X-ray source shown by the cross-hatched circle on the far right of the three X-ray sources selected in FIG. 10A is changed to an X-ray source further to the right, the other X-ray source on the far left is changed so as to substantively proportionately maintain the angles of incidence (FIG. 10C).

Looking at the relation between the X-ray image resulting from the three X-ray sources selected in FIG. 10C and the X-ray image resulting from the three X-ray sources selected in FIG. 10A, the angles of incidence relative to the region of interest are changed. However, the relation of the differences in the angles of incidence of the three selected X-ray sources is substantively maintained. Here, "substantively maintained" denotes the following. If the X-ray sources in the multi X-ray source are arranged equidistantly, the differences of the angles of incidence before and after the selection change cannot be made to completely coincide. However, if the X-ray source arrangement pitch of the multi X-ray source is very small compared with the distance from the multi X-ray source to the object, any difference in the differences of the angles of incidence before and after the selection change can be disregarded. This is referred to as being "substantively maintained."

Note that the relation maintaining mode and the proportion maintaining mode of the second embodiment respectively correspond to control of the collimator 27 in the shifting mode and the rotational mode of the first embodiment. In particular, implementing the second embodiment with the rotational mode of the first embodiment is effective. The relation maintaining mode and the proportion maintaining mode of the second embodiment are, however, not limited to the shifting mode and the rotational mode of the first embodiment.

Hereinabove, the second embodiment was described.

Hereinafter, the superiority of the present invention over the related art will be described.

Conventionally, there were only techniques for coordinating a plurality of C-arm imaging systems in fixed relation in a device having a plurality of C-arms.

Also, the number of X-ray sources of the plurality of imaging systems was commonly two at most, and there was no imaging system capable of having from 10 to 100 X-ray sources, such as the abovementioned first and second embodiments.

Therefore, conventionally, changing the selection of X-ray sources currently selected to X-ray sources at other positions was not necessary in the first place in imaging using a plurality of X-ray sources.

Accordingly, the problems solved by the present invention can be said to be new problems that were not conventionally known.

According to the present invention, control relating to scaling the examination area, shifting the examination region, and changing the examination direction in the case where fluoroscopy is performed after narrowing the examination region in order to reduce radiation exposure to the patient can be favorably performed in an X-ray imaging apparatus provided with a multi X-ray source.

Other Embodiments

Aspects of the present invention can also be realized by a computer of a system or apparatus (or apparatuses such as a CPU or MPU) that reads out and executes a program recorded on a memory apparatus to perform the functions of the above-described embodiments, and by a method, the steps of which are performed by a computer of a system or apparatus by, for example, reading out and executing a program recorded on a memory apparatus to perform the functions of the above-described embodiments. For this purpose, the program is provided to the computer for example via a network or from a recording medium of various types serving as the memory apparatus (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-289173, filed Nov. 11, 2008, which is hereby incorporated by reference herein in its entirety.

The invention claimed is:

1. An X-ray imaging apparatus comprising:
   an X-ray generation unit configured to support a plurality of X-ray targets each of which generates X-rays;
   a shielding member capable of adjusting openings corresponding to the plurality of X-ray targets; and
   a control unit configured to control said shielding member so as to adjust the openings in conjunction with each other in accordance with a plurality of control modes,
   wherein, as a first control mode, said control unit controls said shielding member such that X-rays via the openings irradiate an object in the same direction with each other, and as a second control mode, controls said shielding member such that X-rays via the openings irradiate the object in different directions.

2. The apparatus according to claim 1, wherein, in the first control mode, when the position of a first opening of said shielding member corresponding to a first X-ray target is adjusted, said control unit adjusts the position of a second opening of said shielding member corresponding to a second X-ray target such that the distance and the direction of the second opening with respect to the second X-ray target become identical to the distance and the direction of the first opening with respect to the first X-ray target.

3. The apparatus according to claim 2, wherein, in the second control mode, when an area of the object is irradiated from the first X-ray target via the first opening, said control unit adjusts the position of the second opening is adjusted such that the same area is also irradiated from the second X-ray target via the second opening.

4. The apparatus according to claim 3, wherein, in the first control mode, said control unit controls said shielding member such that X-rays emitted from the plurality of X-ray targets irradiate different areas of the object,
   and wherein, in the second control mode, said control unit controls said shielding member such that X-rays emitted from the plurality of X-ray targets irradiate the same area of the object at different angles.

5. The apparatus according to claim 1, wherein said control unit selects one or more X-ray targets to be used for X-ray irradiation from among the plurality of the X-ray targets.

6. The apparatus according to claim 1, wherein said control unit sequentially changes one or more X-ray targets to be used for X-ray irradiation from among the plurality of X-ray targets.

7. The apparatus according to claim 1, wherein said openings are adjustable in size and/or position, and wherein said shielding member is further capable of adjusting the size of said openings corresponding to the plurality of X-ray targets, and
   wherein said control unit controls said shielding member to adjust the size and/or position of said openings.

8. The apparatus according to claim 3, wherein, in the second control mode, said control unit controls said shielding member and the plurality of X-ray targets such that X-rays emitted from the plurality of X-ray targets irradiate the same area of the object in different directions.

9. The apparatus according to claim 3, wherein said control unit switches between the first control mode and the second control mode.

10. The apparatus according to claim 3, wherein said control unit further includes a third control mode in which X-rays emitted from the plurality of X-ray targets irradiate different areas of the object in different directions.

11. The apparatus according to claim 3, wherein said control unit further includes a fourth control mode in which X-rays emitted from the plurality of X-ray targets irradiate different areas of the object from one of different directions.

12. An X-ray imaging apparatus comprising:
    an X-ray generation unit configured to support a plurality of X-ray targets each of which generates X-rays;
    a shielding member capable of adjusting the size and/or position of openings corresponding to the plurality of X-ray targets; and
    a control unit configured to control said shielding member so as to adjust the openings in conjunction with each other in accordance with a plurality of control modes,
    wherein, as a first control mode, said control unit controls said shielding member such that X-rays via the openings irradiate an object in the same direction with each other, and, as a second control mode, controls said shielding member such that X-rays via the openings irradiate the object in different directions.

* * * * *